United States Patent [19]
Bay et al.

[11] Patent Number: 5,556,971
[45] Date of Patent: Sep. 17, 1996

[54] PROCESS FOR PREPARING ISOCYANATE AND ISOCYANATE-BASED DERIVATIVES OF CERTAIN AMINO-1,3,5-TRIAZINES BY DIRECT PHOSGENATION

[75] Inventors: William E. Bay, Ridgefield; William F. Jacobs, III, Bethel; David Gschneidner, Stamford, all of Conn.; Ram B. Gupta, Bronx, N.Y.

[73] Assignee: Cytec Technology Corp., Wilmington, Del.

[21] Appl. No.: 239,009

[22] Filed: May 6, 1994

[51] Int. Cl.⁶ .................................. C07D 251/54
[52] U.S. Cl. .................. 544/196; 544/196; 544/200; 544/207
[58] Field of Search .................. 544/196, 198, 544/200, 207

[56] References Cited

U.S. PATENT DOCUMENTS

| | | | |
|---|---|---|---|
| 3,732,223 | 5/1973 | Gizycki et al. | 260/249.8 |
| 3,919,221 | 11/1975 | Dazzi | 544/200 |
| 3,983,115 | 9/1976 | Seitz et al. | 260/249.5 |
| 4,444,954 | 4/1984 | Mels et al. | 525/124 |
| 4,939,213 | 7/1990 | Jacobs, III et al. | 525/329.9 |
| 5,084,541 | 1/1992 | Jacobs, III et al. | 544/204 |
| 5,288,865 | 2/1994 | Gupta | 544/200 |

OTHER PUBLICATIONS

E. M. Smolin and L. Rapoport, "S-Triazines and Derivatives", Interscience Publishers Inc., New York, p. 333 (1959).
M. J. Coghlan and B. A. Caley, "Trichloromethyl Carbonate as a Practical Phosgene Source," Tetrahedron Letters, vol. 30, No. 16, pp. 2033–2036 (1989).

*Primary Examiner*—Yogendra N. Gupta
*Attorney, Agent, or Firm*—Bart E. Lerman; Claire M. Schultz; Michael J. Kelly

[57] ABSTRACT

A process is provided for preparing isocyanate and isocyanate-based 1,3,5-triazine derivatives by the direct phosgenation of (at least tris-unsubstituted amino)-1,3,5-triazines.

16 Claims, No Drawings

PROCESS FOR PREPARING ISOCYANATE AND ISOCYANATE-BASED DERIVATIVES OF CERTAIN AMINO-1,3,5-TRIAZINES BY DIRECT PHOSGENATION

BACKGROUND OF THE INVENTION

1. Field of the Invention

This invention relates to the preparation of isocyanate and/or isocyanate-based 1,3,5-triazine derivatives by the direct phosgenation of amino-1,3,5-triazines having at least three unsubstituted amino groups attached to the triazine ring(s).

2. Description of Related Art

Various derivatives of amino-1,3,5-triazines are described in the literature as being utilized in a wide variety of fields. An important use of certain of these derivatives, such as alkoxymethyl derivatives of melamine and guanamines, is as crosslinkers and/or reactive modifiers in curable compositions which contain resins having active hydrogen groups. While alkoxymethylated melamines and guanamines provide excellent results in a number of aspects, they also have the disadvantage of releasing formaldehyde as a volatile by-product under curing conditions. It has long been a desire of industry to find acceptable alternatives which do not emit formaldehyde upon cure.

One such alternative which has shown great promise is carbamate functional 1,3,5-triazines disclosed in the commonly owned U.S. Pat. No. 4,939,213, U.S. Pat. No. 5,084,541, U.S. Pat. No. 5,288,865, U.S. application Ser. No. 07/998,313 (filed Dec. 29, 1992), U.S. application Ser. No. 08/061,905 (filed May 14, 1993), and U.S. application Ser. No. 08/138,581 (filed Oct. 15, 1993), all of which are hereby incorporated by reference herein as if fully set forth. The carbamate functional 1,3,5-triazines disclosed in these references are believed to act in a manner similar to blocked isocyanates, and have been found to be particularly useful as crosslinkers in coating compositions based upon hydroxy functional resins, with the cured coatings possessing a wide range of desirable properties.

One impediment to the commercial use of these carbamate functional 1,3,5-triazines has been that known processes for their preparation have been somewhat cumbersome, difficult and expensive. For example, in previously incorporated U.S. Pat. No. 4,939,213 and U.S. Pat. No. 5,084,541, 1,3,5-triazine carbamates are produced in a two step process by first reacting an amino-1,3,5-triazine with oxalyl chloride to produce an isocyanate which is then converted to the corresponding carbamate by reaction with an alcohol. Further, in previously incorporated U.S. Pat. No. 5,288,865, carbamate functional 1,3,5-triazines are produced in a one-step process by reacting a haloamino-1,3,5-triazine with an acid halide. The primary disadvantages with these processes include the use of somewhat exotic and/or expensive halogenated starting materials and low ultimate yield of the desired products.

Many of these disadvantages have been overcome by the process disclosed in previously incorporated U.S. application Ser. No. 08/061,905, wherein carbamate functional 1,3,5-triazines are produced by reacting an at least bis-amino 1,3,5-triazine with an acyclic organic carbonate in the presence of a strong base.

Another process which overcomes many of these disadvantages is disclosed in previously incorporated U.S. application Ser. No. 08/138,581, wherein isocyanate functional 1,3,5-triazines are produced by the carbonylation of (halo)amino 1,3,5-triazines with carbon monoxide, in the presence of a metal promoter for promoting carbonylation.

It has now been surprisingly discovered that isocyanate functional 1,3,5-triazine derivatives can also be prepared from amino-1,3,5-triazines having at least three unsubstituted amino groups attached to the triazine ring, such as melamine, by direct phosgenation. These isocyanate functional 1,3,5-triazines may be further derivatized by contacting the same with a wide variety of well-known isocyanate-reactive materials. For example, these isocyanates may be readily "blocked" (for example, converted to the corresponding carbamate) by adding a blocking agent (such as a hydroxyl compound) to the isocyanate functional 1,3,5-triazine without isolating it. In addition, these isocyanates may be readily oligomerized by adding a multifunctional isocyanate-reactive compound (for example, a diol or diamine) to the isocyanate functional 1,3,5-triazine without isolating it.

It should be noted that it is generically known to obtain isocyanates by direct phosgenation of amines. It is, however, also well known that the amine functionality of amino-1,3,5-triazines, such as melamine, is not equivalent to other types of typical amine functionality. Significantly, melamines are among the least reactive of the "amines" and the most difficult to functionalize, and their behavior cannot normally be correlated to that of other known amines.

For example, most "typical" amines are highly reactive with acid halides. In a publication by E. M. Smolin and L. Rappaport entitled "S-Triazines and Derivatives," Interscience Publishers Inc., New York, page 333 (1959), it is reported that attempts to react an acid halide with the amino group on a 1,3,5-triazine such as melamine were not successful. Further, attempts to functionalize amino-1,3,5-triazines often results in substitution at the nitrogen on the triazine ring. For example, it is known that the reaction of melamine with alkyl halides, such as allyl chloride, results in alkyl substitution at the nitrogen on the triazine ring resulting in isomeamine derivatives.

Indeed, it is reported in U.S. Pat. No. 3,732,223 that the well-known phosgenation of amines fails to produce isocyanate functionality when applied to amino-1,3,5-triazines. In subsequent U.S. Pat. No. 3,919,221, the phosgenation of amino-1,3,5-triazines having one or two unsubstituted amino groups attached to the triazine ring to obtain monoisocyanate and diisocyanate triazines is reported to occur under certain specified conditions. Both of the above patents are incorporated by reference herein as if fully set forth.

It appears, however, that procedure generically described in previously incorporated U.S. Pat. No. 3,919,221 does not effectively or significantly proceed with amino-1,3,5-triazines having at least three unsubstituted amino groups attached to the triazine ring(s), such as melamine (2,4,6-triamino-1,3,5-triazine). Without wishing to be bound by any particularly theory, it is believed that solubility constraints of these (at least tris-unsubstituted amino)-1,3,5-triazines, in conjunction with the difficulties associated with the functionalization of amino-1,3,5-triazines in general, may hinder the reaction of such compounds with phosgene under the reaction conditions reported in the reference.

Surprisingly, a procedure has now been discovered in which phosgene (and phosgene sources) can readily and effectively be directly reacted with such (at least tris-unsubstituted amino)-1,3,5-triazines (direct phosgenation) to produce the corresponding isocyanate functional 1,3,5-triazine derivatives, which can further be readily and effectively reacted with known isocyanate-reactive materials (such as blocking agents) to produce the corresponding isocyanate-based derivatives thereof.

SUMMARY OF THE INVENTION

In accordance with the present invention, there is provided a process for preparing isocyanate functional derivatives of (at least tris-unsubstituted amino)-1,3,5-triazines comprising, in its overall concept, the steps of:

(a) contacting (i) an (at least tris-unsubstituted amino)-1, 3,5-triazine and (ii) phosgene, in a reaction system, at a temperature, a pressure and for a length of time sufficient to produce an isocyanate functional 1,3,5-triazine derivative and hydrogen chloride; and (b) removing at least a portion of the hydrogen chloride from the reaction system as such hydrogen chloride is generated during the reaction of (i) and (ii).

The isocyanate-based derivatives can be readily produced via known procedures by reacting an isocyanate-reactive material with the isocyanate functional 1,3,5-triazine product formed by the reaction of (i) and (ii).

An important step of the process of the present invention requires that the by-product hydrogen chloride be at least partially removed as it is generated by the reaction of phosgene with the (at least tris-unsubstituted amino)-1,3,5-triazine. This is preferably achieved by conducting the reaction under conditions whereby the by-product hydrogen chloride can be selectively vented from the reaction system. More preferably, the reaction is conducted under pressure and temperature conditions whereby the phosgene is refluxed and the by-product hydrogen chloride is gaseous.

As indicated above, an isocyanate functional 1,3,5-triazine product is produced by contacting (i) and (ii), which may be reacted with isocyanate-reactive materials to produce various isocyanate-based derivatives. For example, the isocyanate groups may be blocked by contacting the isocyanate functional 1,3,5-triazines with known isocyanate blocking agents, such as certain active-hydrogen containing compounds. As another example, oligomers of the isocyanate functional 1,3,5-triazines can be produced by contacting the same with multifunctional isocyanate reactive materials such as diols and diamines. The phrase "isocyanate and/or isocyanate-based" 1,3,5-triazines, in the context of the present invention, includes triazine derivatives having isocyanate functionality, isocyanate-based functionality, or a mixture of isocyanate and isocyanate-based functionality. For example, when a blocking agent is added in an amount which is less than the molar equivalent of the available isocyanate functionality, then a triazine derivative is produced having both isocyanate and blocked-isocyanate functionality.

The process of this invention is advantageous because no exotic and costly starting materials, and particularly no halogenated amino-1,3,5-triazine starting materials, are required. Further, (at least tris-unsubstituted amino)-1,3,5-triazines can, for the first time, be directly phosgenated via generally conventional procedures largely known and currently utilized on large industrial scales, which procedures can readily be modified as required by the present inventive process. Moreover, the (at least tris-unsubstituted amino)-1, 3,5 triazines, such as melamine, can be directly reacted with phosgene, followed by reaction of the isocyanate with any one of a wide variety of well-known isocyanate reactive materials to obtain an isocyanate-based 1,3,5-triazine without handling or isolation of the isocyanate triazine product.

A preferred use for the isocyanate functional 1,3,5-triazines and various derivatives thereof is as a crosslinking agent with polyfunctional active hydrogen containing resins such as hydroxy functional acrylic or polyester resins, for producing curable compositions which have utility in coatings, adhesives, molding and other applications. This and other uses are disclosed in various of the previously incorporated references.

These and other features and advantages of the present invention will be more readily understood by those of ordinary skill in the art from a reading of the following detailed description.

DETAILED DESCRIPTION OF THE PREFERRED EMBODIMENTS

As indicated above, the present invention is a novel process for preparing isocyanate functional 1,3,5-triazines by contacting an (at least tris-unsubstituted amino)-1,3,5-triazine with phosgene. The process is carried out at a temperature, pressure and for a sufficient time, and further under conditions which allow removal of at least a portion, and preferably a substantial portion, of the reaction-generated hydrogen chloride from the reaction system as it is generated, resulting in the formation of the corresponding isocyanate functional 1,3,5-triazines. In general, each unsubstituted amino group on the amino-1,3,5-triazine will be converted to an isocyanate group; consequently, the direct phosgenation of a (tris-unsubstituted amino)-1,3,5-triazine, such as melamine, in accordance with the present invention will result in the corresponding tris-isocyanate product.

When an isocyanate-reactive material such as a well-known isocyanate blocking agent is added subsequent to the formation of the isocyanate functional 1,3,5-triazine, there is obtained the corresponding 1,3,5-triazine with isocyanate-based (blocked isocyanate) functionality. More highly functional derivatives of such isocyanate functional 1,3,5-triazines can also be produced by adding subsequent to the formation of the isocyanate functional 1,3,5-triazine a multifunctional isocyanate reactive material.

The (At Least Tris-Unsubstituted Amino)-1,3,5-Triazine Starting Materials

The (at least tris-unsubstituted amino)-1,3,5-triazine starting materials, such as melamine (2,4,6-triamino-1,3,5-triazine) and oligomers thereof, are well known and readily available. The term "at least tris-unsubstituted amino" in the context of the invention is meant to include a monomeric 1,3,5-triazine having three —$NH_2$ groups attached to the triazine ring (melamine), as well as oligomers of various 1,3,5-triazines (e.g., dimers, trimers and tetramers) having a total of at least three —$NH_2$ groups attached to the triazine rings per molecule. The preferred (at least tris-unsubstituted amino)-1,3,5-triazine starting materials are generally represented by the formula:

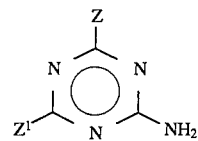

wherein

Z and $Z^1$ are independently selected from the group consisting of —$NH_2$, and a group represented by the formula:

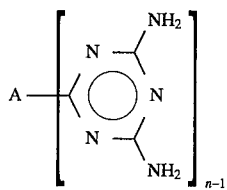

wherein

A is an n functional anchor and n is at least 2.

Preferred for use with the process of the present invention is substantially monomeric melamine, wherein where both Z and $Z^1$ are —$NH_2$.

Also suitable are oligomeric versions of melamine which, as is well-known to those of ordinary skill in the art, may be derived from the self-condensation of melamine or the reaction of melamine with a polyfunctional co-reactant. This oligomeric version is represented when one or both of Z and $Z^1$ are the formula represented above, wherein the group A in the above formula is an n functional anchor which can, for example, be a hydrocarbyl compound residue, an amino compound residue, oxygen or sulfur. "Hydrocarbyl compound residue" in the context of the present invention refers to the residue of compound based on carbon and hydrogen atoms after abstraction of reacted functionality, as well as substituted derivatives thereof.

More preferably, the oligomeric (at least tris-unsubstituted amino)-1,3,5-triazines including the group A have the following general formula:

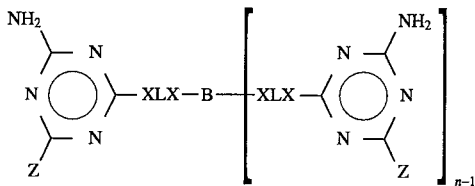

wherein

B is selected from the group consisting of hydrocarbyl compound residue and a hydrocarbyloxy hydrocarbyl compound residue;

each X is independently selected from the group consisting of NH, N(hydrocarbyl), N(hydrocarbyloxy hydrocarbyl), $CH_2O$, S, $CO_2$ and $NHCO_2$;

each L is independently selected from the group consisting of a hydrocarbylene and a hydrocarbyleneoxy hydrocarbyl;

n is at least 2; and

Z is as defined above.

The term "hydrocarbyl" in the context of the present invention, is a group which contains carbon and hydrogen atoms and includes, for example, alkyl, aryl, aralkyl, alkenyl, and substituted derivatives thereof. Likewise, the term "hydrocarbylene" refers to a divalent hydrocarbyl such as, for example, alkylene, arylene, aralkylene, alkenylene, and substituted derivatives thereof.

Phosgene

Phosgene is well-known to those of ordinary skill in the art as being represented by the formula ClC(O)Cl. Phosgene, as defined within the context of this invention, also includes phosgene analogs capable as serving as a phosgene source, as well as phosgene equivalents which are generally well-known to those of ordinary skill in the art. Exemplary phosgene analogs include, without limitation, diphosgene and triphosgene. Diphosgene (trichloromethyl chloroformate) and triphosgene (trichloromethyl carbonate) are represented, respectfully, by the formulas $ClC(O)CCl_3$ and $Cl_3COC(O)OCCl_3$. Triphosgene is known by those skilled in the art to be a phosgene source. See, e.g., M. J. Coghlan and B. A. Caley, "Trichloromethyl Carbonate as a Practical Phosgene Source" Tetrahedron Letters, Vol. 30, No. 16, pp. 2033–2036 (1989). Exemplary phosgene equivalents include, without limitation, N,N'-carbonyldiamidazole and dicyanocarbonyl. The use of phosgene is most preferred in the present invention.

The Isocyanate-Reactive Materials

As mentioned earlier, isocyanate-based 1,3,5-triazine derivatives can readily be produced in accordance with the present invention by post-reacting the isocyanate-functional 1,3,5-triazine with an isocyanate-reactive material such as an active-hydrogen containing compound.

A wide variety of active-hydrogen containing compounds are suitable for use in forming isocyanate-based derivatives, such as carbamates, and are described in detail in the previously incorporated references. For instance, the active-hydrogen containing compounds employed in this process include those known to one skilled in the art which have at least one active-hydrogen moiety selected from the group consisting of carboxyl, hydroxyl, thiol, sulfonamide, amido, primary amine, secondary amine, salts thereof and mixtures thereof. As preferred examples may be mentioned alcohols, phenols, oximes, hydroxamic ethers, lactams and mixtures thereof.

As a specific preferred example, carbamate-functional 1,3,5-triazine derivatives can be formed by reacting the isocyanate-functional triazines with hydroxyl group-containing compounds. As suitable hydroxyl group-containing compounds may be mentioned, for example, straight or branched monohydric or polyhydric alkanols and alkenols having 1 to 20 carbon atoms per molecule, monohydric or polyhydric cycloalkanols and cycloalkenols having 3 to 20 carbon atoms in the molecule, and monohydric and polyhydric arylalkyls having 7 to 20 carbon atoms per molecule. Further, these alcohols may also have a substituent such as a halogen atom, a cyano group, an alkoxy group, a sulfoxide group, a sulfone group, a carbonyl group, an ester group, an ether group and an amide group. Mixtures of the above are also suitable.

Preferred of the above are the aliphatic linear, cyclic, saturated, or unsaturated alcohols having 1 to 8 carbon atoms, as well as mixtures thereof. As specific preferred examples may be mentioned methanol, ethanol, 1-propanol, 2-propanol, 1-butanol, 2-butanol, iso-butanol, tert-butanol, pentanol, hexanol, cyclohexanol, heptanol, octanol, ethylhexyl alcohol, benzyl alcohol, allyl alcohol, ethylene chlorohydrin, ethylene glycol, propylene glycol, 1,3-propanediol, 1,4-butanediol, ethoxyethanol, hydroxyethoxyethanol, 1-methoxy-2-propanol and mixtures thereof.

Phenols are also suitable as the hydroxyl group-containing compound. As specific examples may be mentioned phenol, various alkyl phenols, various alkoxy phenols, various halogenated phenols, dihydroxybenzene, 4,4-dihydroxydiphenylmethane, various bisphenols such as bisphenol-A, and hydroxynaphthalenes. As specific preferred examples may be mentioned phenol, 2-methyl phenol, 3-methyl phenol, 4-methyl phenol, 2-chlorophenol, 3-chlorophenol, 4-chlorophenol, catechol, resorcinol, hydroquinone, and mixtures thereof.

Many of the aforementioned hydroxyl group-containing compounds are well-known isocyanate blocking agents. Other well-known isocyanate blocking agents are also suitable for use herein, and include, for example, those blocking groups which deblock at relatively low temperatures, e.g., below about 125° C., such as an oxime of an aldehyde or ketone (e.g., methylethyl-ketoxime, acetone oxime and cyclohexanone oxime), lactam (e.g., caprolactam), hydroxamic acid ester, imidazole, pyrazole, N-hydroxyimide (e.g., N-hydroxyphthalimide), dimethylamine, or other blocking groups such as recited in U.S. Pat. No. 4,444,954 the pertinent portions of which are incorporated by reference herein as if fully set forth.

For use as a crosslinking agent as described in various of the previously incorporated reference, most preferred for the isocyanate-reactive compound are aliphatic alcohols and ether-alcohols having 1 to 18 carbons, such as methanol, ethanol, isopropanol, propanol, isobutanol, n-butanol, t-butanol, pentanol, hexanol, heptanol, octanol, nonanol, decanol, lauryl alcohol, 2-ethyl hexanol, alkyl alcohol, glycidol, stearyl alcohol, ethoxyethanol and 1-methoxy-2-propanol.

Process Conditions

In the process of the present invention, the (at least tris-unsubstituted amino)-1,3,5-triazine and phosgene (or phosgene source or equivalent) are contacted in a reaction system at a temperature, pressure, and length of time sufficient to produce the desired isocyanate- functional 1,3,5-triazine. Significantly, at least a portion (and preferably a substantial portion) of the hydrogen chloride generated from the reaction of the components is removed from the reaction system as it is generated during the reaction. The hydrogen chloride by-product can be removed from the reaction system by venting or by the use of a hydrogen chloride scavenger (preferably which does not release water) such as, for example, calcium oxide or other Group II oxides. Preferably, the components are contacted under conditions whereby the hydrogen chloride is gaseous while the phosgene is refluxed, with the removal of the hydrogen chloride being facilitated by passing an inert gas, such as argon or nitrogen, through the pressurized and heated reaction system during the reaction.

The relative amounts of the (at least tris-unsubstituted amino)-1,3,5-triazine and phosgene employed in the process is generally in the range of about 1:3 to about 1:250, and most preferably in the range of about 1:10 to about 1:30, on a weight basis.

The reaction system of the present invention is not limiting, and can be any reaction system, such as a vessel or container, which can be subject to the conditions required to obtain the desired isocyanate-functional 1,3,5-triazine. The reaction system must also include a means for removing the hydrogen chloride by-product during the reaction of the components. Such means for removal of hydrogen chloride can include, for example, venting with inert gases or the use of hydrogen chloride scavengers. An exemplary system is set forth in Example 1 described herein.

The reaction components are preferably contacted under temperature and pressure conditions at which the by-product hydrogen chloride is gaseous and the phosgene is refluxed during the reaction. Preferably, the reaction temperature ranges from above the critical temperature of hydrogen chloride (about 51.4° C.) up to the critical temperature of phosgene (about 182° C.), and more preferably from about 100° C. to about 120° C. In addition, the reaction of the components is preferably conducted at a pressure in the range from about 50 psig to about 1000 psig, and more preferably from about 100 psig to about 200 psig, depending upon the reaction temperature. At these temperatures and pressures, the reaction has been found to produce isocyanate-functional 1,3,5-triazine in a period of time ranging from about 6 hours to about 72 hours.

It is preferred to conduct the reaction in the presence of a liquid medium which is not readily reactive with phosgene (and preferably inert under reaction conditions) such as, for example, nitrobenzene, chlorobenzene, dichlorobenzene, various ethers and polyethers, as well as mixtures thereof. The reaction may be aided by the inclusion of a catalyst in the reaction mixture such as, for example, molecular halides and phosphorous halides.

As previously indicated, to obtain significant conversions at least a portion of the generated hydrogen chloride is removed from the reaction system as it is generated during the reaction. Most preferably, the removal of the reaction-generated hydrogen chloride is achieved by pressurizing the reaction system with an inert gas and heating the reaction components to a temperature which results in the selective distillation of mostly hydrogen chloride and not phosgene. The distilled hydrogen chloride is preferably removed from the reaction system by venting the system with an inert gas, such as argon or nitrogen. The temperature of the reaction components and the pressure of the reaction systems may be readily adjusted by those skilled in the art to maximize the removal of hydrogen chloride and minimize the loss of phosgene during the reaction.

The isocyanate-functional 1,3,5-triazine prepared by the above-described process may subsequently be reacted with the isocyanate-reactive material as described in various of the previously incorporated references. Generally, the isocyanate-functional 1,3,5-triazine and isocyanate-reactive material may be reacted at temperatures ranging from about −20° C. to about 200° C., and for varying times, depending on the isocyanate-reactive material. For most suitable blocking agents, the components are reacted at a temperatures ranging from about 20° C. to about 40° C. when adding the blocking agents. Such blocking reaction is carried out to substantial completion, generally for a time ranging from about 10 minute to about 2 hours. The resulting isocyanate-based 1,3,5-triazines can be isolated in any desired manner, such as by filtration and distillation of the solvent.

The relative amount of isocyanate blocking agent material added to the isocyanate-functional 1,3,5-triazine is generally in the range of about 3:1 to about 30:1 equivalents of isocyanate reactive functionality per isocyanate group. Preferably, the ratio is in the range of about 3:1 to about 5:1 on such equivalent basis.

If the active-hydrogen containing compound added to the reaction is less than the molar equivalent of available isocyanate functionality, then the resulting 1,3,5-triazine will have a mixture of isocyanate and isocyanate-based functionality. When utilized as a "blocked isocyanate" crosslinking agent, it is preferred to add an amount of blocking agent which will react to form a fully blocked-isocyanate functional 1,3,5-triazine.

The examples which follow are intended as an illustration of certain preferred embodiments of the invention, and no limitation of the invention is implied.

EXAMPLE 1

Preparation of Tris-n-Butylcarbamoyl-1,3,5-Triazine by Direct Phosgenation of Melamine and the Addition of N-Butanol One end of a 22 mm diameter, 285 mm long, heavy wall quartz tube was fitted with a Hastelloy C-276 end cap. The other end of the tube was flame sealed closed into a rounded bottom. A 35 mm diameter, 90 mm long water condenser was positioned concentrically onto the outside of the quartz tube approximately 40 mm from the closed end. This condenser was constructed as follows. Rubber stoppers were placed into either end of a 35 mm diameter, 90 mm long section of glass tubing. This section of glass tubing had water inlet/outlet connections near each end. Each of the rubber stoppers had been bored through the center with a single 22 mm diameter hole which the quartz tube was pushed through so that the rubber stoppers formed a seal between the outside of the quartz tube and the inside of the condenser jacket. The Hastelloy end cap had two ⅛ NPT threaded connections. A pressure regulated, dry argon source was attached to the inlet connection through a stainless steel metering valve. The outlet connection was attached to an electronic, recording pressure transducer and a second stainless steel metering valve by means of a tee. The quartz tube was charged with melamine (97 mg) and nitrobenzene (2 ml). A small Teflon coated, magnetic stirring bar was placed inside the quartz tube and the tube clamped vertically in a fume hood so that the Hastelloy end cap was at the top of the quartz tube reactor. The argon inlet valve was closed and the reaction set up attached to a vacuum manifold through the outlet valve. The reaction mixture of melamine and nitrobenzene was frozen by immersing the end of the reaction tube in a slurry of dry ice and acetone. A cylinder of phosgene was attached to the vacuum manifold. The quartz reaction tube and all connecting lines including those between the phosgene cylinder and vacuum manifold were evacuated. The valve on the vacuum manifold leading to the vacuum pump was closed and the phosgene cylinder valve opened slowly. Approximately 2 ml of phosgene was condensed into the reactor. The phosgene cylinder valve and reactor outlet valve were closed. The dry ice acetone slurry was removed from around the end of the reaction tube and the reaction mixture allowed to warm to room temperature. The vacuum manifold and connecting lines were flushed with dry nitrogen into a caustic scrubber. The reactor was disconnected from the vacuum manifold. The outlet valve from the reactor was attached to a caustic scrubber. The argon inlet valve on the reactor was opened and the pressure adjusted to 175 psig. The outlet valve on the reactor was opened slightly so that a flow of 20 to 30 ml per minute of argon flowed through the reactor above the condenser into the caustic scrubber. The water flow through the condenser was started. The reaction mixture was heated to reflux by placing the lower end of the reactor in a 100° C. oil bath. The reaction mixture was stirred with a magnetic stirrer placed under the oil bath. Stirring and refluxing were continued for 62 hours. The water flow through the condenser was stopped. The reactor outlet valve was opened and the argon inlet valve used to control the flow of argon so that the excess phosgene was vented into the caustic scrubber. The reaction mixture was stirred and heated with the 100° C. oil bath for 15 minutes after the reaction mixture quit bubbling from the boiling off of the volatile components of the reaction mixture. The oil bath was lowered and the reaction mixture allowed to cool to room temperature. The Hastelloy cap was temporarily removed and n-butanol (2 ml) added with stirring. The oil bath was raised and the reaction mixture heated with stirring for an additional 15 minutes after the n-butanol addition. The reaction mixture was cooled and filtered. The excess solvent and n-butanol were stripped from the filtrate at room temperature under high vacuum.

The remaining light tan, solid residue (41 mg) was analyzed by HPLC and found to be mostly trisbutylcarbamoyltriazine.

COMPARATIVE EXAMPLE 1

The reactor described in EXAMPLE 1 was charged with melamine (96 mg) and nitrobenzene (2 ml). The outlet valve of the charged reactor was attached to a vacuum manifold. The slurry was frozen in dry ice acetone and the reactor evacuated. A cylinder of hydrogen chloride was attached to the reactor inlet valve and the headspace of the reactor filled with hydrogen chloride. The reaction mixture was allowed to warm to room temperature and the hydrogen chloride pressure adjusted to 5 psig. The reactor inlet and the outlet valves were closed. The hydrogen chloride cylinder was disconnected from the inlet valve and replaced with a pressure regulated source of argon. The reaction mixture was frozen with liquid nitrogen. A cylinder of phosgene was attached to the vacuum manifold. The vacuum manifold and all connecting lines were evacuated. The valve leading to the vacuum pump was closed. The phosgene cylinder valve was opened and the reactor outlet valve (now serving as an inlet) was cautiously opened until approximately 2 ml of phosgene had condensed into the reactor. The phosgene cylinder valve and the reactor outlet valve were closed. The vacuum manifold and all connecting lines were flushed with dry nitrogen into a caustic scrubber. The reactor was disconnected from the vacuum manifold. The liquid nitrogen bath was removed from the reactor and the contents of the reactor allowed to warm to room temperature. The argon inlet valve on the reactor was opened and the pressure adjusted to 175 psig. The outlet valve on the reactor remained closed. The water flow through the condenser was started. The reaction mixture was heated to reflux by placing the lower end of the reactor in a 100° C. oil bath. The reaction mixture was stirred with a magnetic stirrer placed under the oil bath. Stirring and refluxing were continued for 66.5 hours. The water flow through the condenser was stopped. The reactor outlet was attached to a caustic scrubber. The reactor outlet valve was opened and the argon inlet valve used to control the flow of argon so that the excess phosgene was vented into the caustic scrubber. The reaction mixture was stirred and heated with the 100° C. oil bath for 15 minutes after the reaction mixture quit bubbling from the boiling off of the volatile components of the reaction mixture. The oil bath was lowered and the reaction mixture allowed to cool to room temperature. The Hastelloy cap was temporarily removed and n-butanol (2 ml) added with stirring. The oil bath was raised and the reaction mixture heated with stirring for an additional 20 minutes after the n-butanol addition. The reaction mixture was cooled and filtered. The excess solvent and n-butanol were stripped from the filtrate at room temperature under high vacuum. Very little residue remained. HPLC analysis of this residue did not detect the presence of trisbutylcarbamoyltriazine.

COMPARATIVE EXAMPLE 2

A 25 ml 3-neck round bottom flask was fitted with a dry ice condenser and a magnetic stirrer. The flask was also connected to a nitrogen source and a nitrogen atmosphere was maintained at ambient pressure. The flask was charged with melamine (1 gram). Phosgene (10 ml) was then condensed into the flask. The resulting slurry was stirred for 7 hours at a reflux temperature of phosgene. The phosgene was then vented to a scrubber. N-Butanol was then added to the reaction mixture. Analysis of the residue showed no trisbutylcarbamoyl-1,3,5-triazine.

COMPARATIVE EXAMPLE 3

Melamine (1.5 grams) and nitrobenzene (20 ml) were mixed in a 110 ml Hastelloy c-276 can. The can was sealed and placed inside a FIKE Vent Sizing Package. The can was cooled with dry ice and evacuated. Phosgene (20 grams) was condensed into the can. The dry ice was allowed to evaporate and the can heated to 100° C. for 3 hours and 20 minutes. The pressure in the reaction vessel rose to 102 psig. Thereafter, the heat was turned off and the vessel vented. n-Butanol (10 ml) was injected into the reactor. HPLC analysis of the reaction mixture revealed no detectable trisbutylcarbamoyl-1,3,5-triazine.

Other variations and modifications of this invention will be obvious to those skilled in this art. This invention is not limited except as set forth in the following claims.

We claim:

1. A process for preparing isocyanate functional derivatives of (at least tris-unsubstituted amino)-1,3,5-triazines comprising the steps of:
   (a) contacting (i) an (at least tris-unsubstituted amino)-1,3,5-triazine comprising melamine or an oligomer thereof and (ii) phosgene, in a reaction system, at a temperature, a pressure and for a length of time sufficient to produce an isocyanate functional 1,3,5-triazine derivative and hydrogen chloride; and
   (b) removing hydrogen chloride from the reaction system as such is generated during the course of the reaction of (i) and (ii).

2. The process of claim 1, wherein the reaction of (i) and (ii) is conducted under conditions whereby the hydrogen chloride is gaseous and the phosgene is refluxed.

3. The process of claim 2, wherein the reaction of (i) and (ii) is conducted at a temperature above the critical temperature of hydrogen chloride and below the critical temperature of phosgene.

4. The process of claim 1, wherein a substantial portion of the hydrogen chloride is removed from the reaction system as such hydrogen chloride is generated during the reaction of (i) and (ii).

5. The process of claim 1, wherein the removing step (b) comprises venting the hydrogen chloride from the reaction system.

6. The process of claim 4, wherein the hydrogen chloride is vented from the reaction system with an inert gas.

7. The process of claim 5, wherein the inert gas is argon or nitrogen.

8. The process of claim 1, wherein the relative amounts of the (at least tris-unsubstituted amino)-1,3,5-triazine and phosgene employed in the process is generally in the range of about 1:3 to about 1:250 on a weight basis.

9. A process for preparing isocyanate-based derivatives of (at least tris-unsubstituted amino)-1,3,5-triazines comprising the steps of:
   (a) contacting (i) an (at least tris-unsubstituted amino)-1,3,5-triazine comprising melamine or an oligomer thereof and (ii) phosgene, in a reaction system, at a temperature, a pressure and for a length of time sufficient to produce an isocyanate functional 1,3,5-triazine derivative and hydrogen chloride;
   (b) removing the by product hydrogen chloride from the reaction system as such is generated during the course of the reaction of (i) and (ii); and
   (c) reacting an isocyanate-reactive material with the isocyanate functional 1,3,5-triazine derivative formed by the reaction of (i) and (ii).

10. The process of claim 9, wherein the reaction of (i) and (ii) is conducted under conditions whereby the hydrogen chloride is gaseous and the phosgene is refluxed.

11. The process of claim 10, wherein the reaction of (i) and (ii) is conducted at a temperature above the critical temperature of hydrogen chloride and below the critical temperature of phosgene.

12. The process of claim 9, wherein a substantial portion of the hydrogen chloride is removed from the reaction system as such hydrogen chloride is generated during the reaction of (i) and (ii).

13. The process of claim 9, wherein the relative amounts of the (at least tris-unsubstituted amino)-1,3,5-triazine and phosgene employed in the process is generally in the range of about 1:3 to about 1:250 on a weight basis.

14. The process according to claim 9, wherein the isocyanate-reactive material is an active-hydrogen containing compound selected from the group consisting of alcohols, phenols, oximes, hydroxamic acid ethers, lactams and mixtures thereof.

15. The process according to claim 14, wherein the active-hydrogen containing compound comprises an alcohols selected from the group consisting of methanol, ethanol, 1-propanol, 2-propanol, 1-butanol, 2-butanol, iso-butanol, tert-butanol, pentanol, hexanol, cyclo-hexanol, heptanol, octanol, ethylhexyl alcohol, benzyl alcohol, allyl alcohol, ethylene chlorohydrin, ethylene glycol, propylene glycol, 1,3-propanediol, 1,4-butanediol, ethoxyethanol, hydroxyethoxyethanol, 1-methoxy-2-propanol and mixtures thereof.

16. The process of claim 9, wherein the isocyanate-reactive material is an isocyanate blocking agent.

* * * * *